United States Patent [19]

Wetzler et al.

[11] 4,145,553
[45] Mar. 20, 1979

[54] MANUFACTURE OF 4-NITROIMIDAZOLES

[75] Inventors: Matthias Wetzler, Ludwigshafen; Toni Dockner, Meckenheim, both of Fed. Rep. of Germany

[73] Assignee: BASF Aktiengesellschaft, Ludwigshafen, Fed. Rep. of Germany

[21] Appl. No.: 834,414

[22] Filed: Sep. 19, 1977

[30] Foreign Application Priority Data

Oct. 7, 1976 [DE] Fed. Rep. of Germany ....... 2645172

[51] Int. Cl.² .................................... C07D 233/02
[52] U.S. Cl. ................................ 548/338; 260/688
[58] Field of Search ................. 260/309, 644, 688; 548/338

[56] References Cited

FOREIGN PATENT DOCUMENTS 1278679  6/1972  United Kingdom.
1411476 10/1975  United Kingdom.

*Primary Examiner*—Leland A. Sebastian
*Attorney, Agent, or Firm*—Keil & Witherspoon

[57] ABSTRACT

Manufacture of 4-nitroimidazoles by nitrating imidazoles with nitric acid in the presence of urea while at the same time removing water from the mixture by distillation.

The compounds which can be manufactured by the process of the invention are catalysts for polymerization reactions and condensation reactions, especially for reactions with epoxides, the aldol condensation, the manufacture of polyurethanes, condensation reactions with malonic esters or acetoacetic esters and intermediates for the manufacture of dyes, textile auxiliaries and insecticides.

10 Claims, No Drawings

MANUFACTURE OF 4-NITROIMIDAZOLES

The present invention relates to a process for the manufacture of 4-nitroimidazoles by nitrating imidazoles with nitric acid in the presence of urea whilst at the same time removing water from the reaction mixture by distillation.

The nitration of 2-methylimidazole with concentrated sulfuric acid and concentrated nitric acid is disclosed in "Arzneimittelforschung" 1966, pages 23–29. By evaporating the sulfuric acid solution of 2-methylimidazole, the sulfate is obtained undiluted; this compound is then introduced into nitric acid of density 1.38, whilst carefully cooling the mixture, and finally nitric acid of density 1.49, followed by sulfuric acid of density 1.83, is added. The nitration takes place at 140° C. The yields of end product are unsatisfactory and the process is not sufficiently economical and safe for industrial production.

German Laid-Open Specification DOS 1,808,104 discloses that 2-alkyl-4-nitroimidazoles can be manufactured advantageously by nitrating 2-alkyl-imidazoles with nitric acid in the presence of sulfuric acid at an elevated temperature if the reaction is carried out in the presence of urea. Regarding the reaction temperature, the publication expressly states that the reaction is in general carried out at from 40° to 200° C., preferably from 120° to 150° C.; the Examples refer to temperatures from 135° to 140° C. Nitric acid of density from 1.37 to 1.52, preferably of density 1.52, is used. The stated nitric acid densities correspond to a nitric acid concentration (at 15° C.) of from 60 to 100 percent by weight. All the Examples illustrate the use of nitric acid of density 1.52. Substantial difficulties, particularly in operation on an industrial scale, are involved in the storage and metering of 100 percent strength by weight nitric acid in respect of the material from which to construct the apparatus. Whilst when using, for example, 65 percent strength by weight nitric acid, certain chromium-nickel-iron alloys can be used as the material, it is necessary, because of corrosion, to resort to other, substantially more expensive material, for example tantalum alloys, enamel or titanium alloys, when using 100 percent strength by weight nitric acid. If, on the other hand, the process is carried out with nitric acid containing water, eg. nitric acid of 65 percent strength by weight, at from 130° to 140° C., unsatisfactory yields of end product are obtained.

German Laid-Open Application DOS 2,208,924 discloses an improvement to the process of German Laid-Open Application DOS 1,808,104, and uses reaction temperatures above 200° C. All the Examples are carried out with 65 percent strength by weight nitric acid of density 1.40. A disadvantage of this process is that the reactors used can in general not contain more than 0.030 tonne of reaction mixture. The very high heat of reaction of the nitration, resulting from the high rate of reaction at above 200° C., would require such a high ratio of heat exchange surface to volume as to make the construction of such reactors uneconomical and technically difficult. If the heat is not removed sufficiently rapidly, it builds up in the reactor and results in explosion hazards.

We have found that 4-nitroimidazoles of the formula

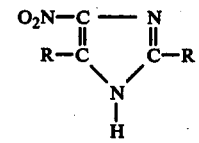

where the individual radicals R may be identical or different and each is hydrogen or an aliphatic radical, may be obtained in an advantageous manner by nitrating imidazoles with nitric acid in the presence of sulfuric acid and urea at an elevated temperature if imidazoles of the formula

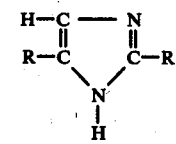

where R has the above meaning, are used for the reaction and water is removed from the reaction mixture by distillation during the reaction.

If 2-methyl-imidazole is used, the reaction can be represented by the following equation:

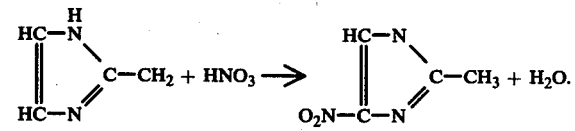

Compared to the conventional processes, the process of the invention surprisingly gives 4-nitroimidazoles is better yield and higher purity and by a simple method which when carried out on an industrial scale is more economical or safer. Aqueous nitric acid can be used on an industrial scale. The reaction can be carried out at relatively low temperature and also in sizable reactors, containing more than 2 tonnes of reaction mixture. It is an advantage over the conventional processes that the nitric acid entrained when removing water by distillation does not have to be neutralized and can be recycled to the reaction. All these advantageous results are surprising in view of the prior art, since it is known (Ullmanns Encyklopädie der technischen Chemie, volume 15, pages 35 to 37) that mixtures of water and nitric acid give an azeotrope (at atmospheric pressure) containing 68 percent by weight of nitric acid and on distilling nitric acid of more than 68 percent strength by weight the concentration of the acid in the distillation vessel correspondingly decreases from its initial value. On distilling mixtures of nitric acid and concentrated sulfuric acid, a high proportion of nitric acid passes into the distillate; in fact, such a process is used for the manufacture of very concentrated nitric acid. Thus, the distillation of mixtures of 60 percent strength by weight nitric acid and 96 percent strength by weight sulfuric acid gives a distillate containing 99 percent by weight of nitric acid. A mixture of 40 percent by weight of nitric acid, 40 percent by weight of sulfuric acid and 20 percent by weight of water gives a distillate containing 95 percent by weight of nitric acid (loc.cit., page 36, paragraph 2). Hence, at the initial concentrations preferred for the process of the invention, ie. from 35 to 40 percent by weight of sulfuric acid, from 27 to 35 percent by weight of nitric acid and from 16 to 20 percent by weight of water, the distillate would have been expected to contain from 95 to 99 percent by weight of nitric acid and hence, compared to the prior art, lower yields, greater losses of acid, uneconomical and complicated operation, longer reaction times and, associated therewith, increased formation of by-products, and adverse conditions for the operatives, due to the high proportion of nitric acid and nitric oxides distilled off, would have been expected. Surprisingly, only a small proportion of nitric acid is removed and the distillate obtained in general contains from 0 to 40 percent by weight of nitric acid, this concentration decreasing with increasing height of the distillation column.

Preferred starting materials II and, accordingly, preferred end products I are those where the individual radicals R may be identical or different and each is hydrogen or linear or branched alkyl of 1 to 6 carbon atoms. Because of the tautomerism of the imidazole, the substituent described as being in the 5-position of the molecule may alternatively be described as being in the 4-position. The above radicals may furthermore be substituted by organic groups which are inert under the reaction conditions, eg. alkyl of 1 to 4 carbon atoms, or by nitro.

Examples of suitable starting materials are imidazole which is unsubstituted, or monosubstituted in the 2-position, 4-position or 5-position by methyl, ethyl, n-propyl, isopropyl, n-butyl, sec.-butyl, tert.-butyl, or isobutyl, or is disubstituted in the 2,4-position or 2,5-position by two methyl, ethyl, n-propyl, isopropyl, n-butyl, iso-butyl, sec.-butyl or tert.-butyl groups, and disubstituted imidazoles which contain two of the above radicals which are however, different from one another, eg. 2-methyl-4-ethyl-imidazole, 2-neopentyl-4-ethyl-imidazole and corresponding imidazoles disubstituted in the 2,5-position.

The nitration of the 2-alkylimidazoles is carried out with nitric acid in the presence of sulfuric acid, as a rule highly concentrated or fuming sulfuric acid. In general, the nitric acid has a density of from 1.38 to 1.52, preferably from 1.38 to 1.42, and the sulfuric acid has a density of from 1.82 to 1.87, preferably 1.84. Advantageously, the nitrating acid, ie. the mixture of nitric acid and sulfuric acid, contains from 0.2 to 2 moles of nitric acid per mole of sulfuric acid. As a rule, from 1 to 5 moles, preferably from 3 to 4 moles, of nitric acid are used per mole of starting material II. Advantageous nitrating mixtures contain from 20 to 40, preferably from 27 to 35 percent by weight of nitric acid (taken to be of 100 percent strength), from 20 to 40, preferably from 35 to 40, percent by weight of sulfuric acid (taken to be of 100 percent strength) and from 15 to 45, preferably from 16 to 20, percent by weight of water. In preparing the starting mixture, all the water, or a part thereof, may be added separately from the other components of the mixture, but as a rule it is more advantageous to add the water in the form of sulfuric acid containing an appropriate amount of water and/or, in particular, nitric acid containing an appropriate amount of water. Instead of nitric acid, compounds which form nitric acid in the reaction mixture, for example inorganic nitrates, such as sodium nitrate and potassium nitrate, may be used, in appropriate amounts.

The urea is in general used in an amount of from 10 to 100, preferably from 45 to 55, percent by weight, based on the imidazole II. The reaction is as a rule carried out at a temperature below 200° C., preferably at from 110° to 160° C., advantageously at from 120° to 140° C. and especially at from 122° to 138° C., under atmospheric pressure, batchwise or continuously.

The reaction mixture can be distilled during a part of the reaction time, advantageously during from 30 to 100% of the reaction time, in the 1st or 2nd part of the reaction time or, more advantageously, during the entire reaction time. Reaction vessels which may be used are a wide range of distillation equipment, eg. sieve tray, Oldershaw, glass tray, bubble-cap tray or valve tray columns, falling film distillation equipment or, in continuous operation, also multi-stage reactors, eg. a cascade reactor, advantageously employing 3 stages, or a series of stirred kettles or tray columns, eg. sieve tray, Oldershaw, glass tray, bubble-cap tray or valve tray columns.

In addition to the water referred to above, present in the starting mixture, water of reaction forms during the reaction. By distillation during the reaction, all or part of the water in the mixture can be removed; advantageously, from 5 to 90, preferably from 60 to 90, percent by weight, based on the total amount of initially added water plus water formed during the reaction, is removed. In general, from 0 to 40, preferably from 0 to 30, percent by weight of nitric acid, based on the amount of nitric acid present in the starting mixture, is also removed by the distillation.

The reaction may be carried out as follows: a mixture of the imidazole II, urea, sulfuric acid and nitric acid is heated to the reaction temperature and is then kept thereat for from 4 to 10, preferably from 5 to 6.5, hours whilst at the same time distilling a mixture of water and nitric acid. The reaction mixture is then poured onto ice or water. The acid in the mixture is neutralized with alkali, preferably ammonia, to pH 3–4, and the end product which thereupon separates out is filtered off and is either crystallized from water, dimethylformamide or formic acid or is purified by dissolving it in dilute hydrochloric acid and precipitating it with dilute ammonia solution. The distillate of aqueous nitric acid is used for a further reaction.

The reaction can also be carried out continuously by an appropriate method, eg. by feeding the above mixture containing sulfuric acid, and the nitric acid, separately to a heated reaction cascade equipped with a distillation receiver, and mixing the two components, in the form of a thin jet, thoroughly with one another. Advantageously, the reaction mixture is left in the cascade at the reaction temperature for from 10 to 20 hours and is then worked up as described. Where appropriate, inert gases, eg. nitrogen, can be passed through the reaction space to remove nitrous fumes formed.

The compounds which may be manufactured by the process of the invention are catalysts for polymerization reactions and condensation reactions, especially for reactions with epoxides, the aldol condensation, the manufacture of polyurethanes and condensation reactions with malonic esters or acetoacetic esters, eg. diethyl malonate or ethyl acetoacetate, and intermediates for the manufacture of dyes, textile auxiliaries and insecticides. Regarding their use, reference may be made to the above publications.

In the Examples which follow, parts are by weight.

EXAMPLE 1

A mixture of 330 parts of sulfuric acid (36 percent by weight), 100 parts of 2-methylimidazole, 50 parts of urea, 283 parts of nitric acid (31 percent by weight) and 153 parts of water is kept for 6.5 hours in a distillation vessel, equipped with a stirrer, at from 123° to 130° C. During the reaction, 20 parts of 30 percent strength by weight nitric acid distill off. The reaction mixture is then diluted with a 3.5-fold volume of water whilst cooling and is neutralized to pH 3–4 with ammonia solution. The 2-methyl-4-nitroimidazole which separates out is centrifuged off, washed, dried and recrystallized from water. 138 parts of 2-methyl-4-nitroimidazole (89.0% of theory) of melting point 145°–146° C. are obtained.

EXAMPLE 2

A mixture of 2,730 parts of sulfuric acid (35 percent by weight), 835 parts of 2-methylimidazole, 410 parts of urea, 2,465 parts of nitric acid (32 percent by weight) and 1,350 parts of water is reacted continuously in a three-stage cascade (consisting of 3 reactors each with a distillation column and reflux condenser) for 6 hours at from 125° to 133° C. During the reaction, 1,130 parts of 14.4 percent strength by weight nitric acid distill off. The reaction mixture is then diluted with a 3.5-fold volume of water whilst cooling and is neutralized to pH 3–4 with ammonia solution. The 2-methyl-4-nitroimidazole which separates out is centrifuged off, washed, dried and recrystallized from water. 1,060 parts of 2-methyl-4-nitroimidazole (81.5% of theory) of melting point 145°–146° C. are obtained.

EXAMPLE 3

A mixture of 3,735 parts of sulfuric acid (35.5 percent by weight), 1,135 parts of 2-methylimidazole, 565 parts of urea, 3,495 parts of nitric acid (33 percent by weight) and 1,625 parts of water is reacted continuously in a three-stage cascade (consisting of 3 reactors each with a distillation column and reflux condenser) for 6 hours at from 125° to 130° C. During the reaction, 2,088 parts of 33 percent strength by weight nitric acid distil off. The reaction mixture is then diluted with a 3.5-fold volume of water whilst cooling and is neutralized to pH 3–4 with ammonia solution. The 2-methyl-4-nitroimidazole which separates out is centrifuged off, washed, dried and recrystallized from water. 1,475 parts of 2-methyl-4-nitroimidazole (83.5% of theory) of melting point 145°–146° C. are obtained.

We claim:

1. A process for the manufacture of a 4-nitroimidazole of the formula

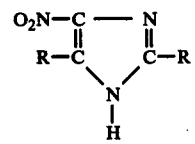

where the individual radicals R are identical or different and each is hydrogen or an aliphatic radical which comprises: nitrating an imidazole with nitric acid in the presence of sulfuric acid and urea at an elevated temperature, in which an imidazole of the formula

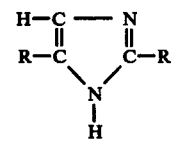

where R has the above meaning, is used for the reaction and water is removed from the reaction mixture by distillation during the reaction.

2. A process as set forth in claim 1, in which the reaction is carried out with nitric acid of density from 1.38 to 1.52 and sulfuric acid of density from 1.82 to 1.87.

3. A process as set forth in claim 1, in which the reaction is carried out with from 0.2 to 2 moles of nitric acid per mole of sulfuric acid and from 1 to 5 moles of nitric acid per mole of starting material II.

4. A process as set forth in claim 1, in which the reaction is carried out with from 10 to 100 percent by weight of urea, based on the imidazole II.

5. A process as set forth in claim 1, in which the reaction is carried out at from 110° to 160° C.

6. A process as set forth in claim 1, in which the reaction is carried out at from 120° to 140° C.

7. A process as set forth in claim 1, in which the aliphatic radical is a linear or branched alkyl of 1 to 6 carbon atoms.

8. A process as set forth in claim 1, in which the water distillate is removed through a distillation column and contains from 0 to 40% by weight of nitric acid.

9. A process as set forth in claim 8, in which the concentration of nitric acid in the distillate decreases with increasing height of the distillation column.

10. A process as set forth in claim 1, in which 5 to 90% by weight of water, based on the total amount of initially added water plus water formed during the reaction, is removed from the reaction mixture.

* * * * *